United States Patent [19]
Yamato et al.

[11] 3,954,897
[45] May 4, 1976

[54] PROCESS FOR PREPARING POLYMER OILS AND POLYMER OILS PREPARED THEREBY

[75] Inventors: Motoyuki Yamato; Hiroshi Yaginuma; Ryuji Kita, all of Kawasaki, Japan

[73] Assignee: Nippon Zeon Co., Ltd., Tokyo, Japan

[22] Filed: Sept. 16, 1974

[21] Appl. No.: 506,074

[30] Foreign Application Priority Data
Sept. 19, 1973 Japan............................. 48-105640

[52] U.S. Cl. .................... 260/676 R; 260/683.15 B; 260/683.9; 424/358
[51] Int. Cl.² .......................................... C07C 5/04
[58] Field of Search ............... 260/677 R, 683.15 R, 260/666 R, 683.9, 683.1, 683.15 B; 424/83, 358; 252/59

[56] References Cited
UNITED STATES PATENTS
3,149,178   9/1964   Hamilton et al. ................ 260/683.9
3,215,599  11/1965   Thau ..................................... 424/83

OTHER PUBLICATIONS

Industrial and Engineering Chemistry, Vol. 44, No. 7, "Catalyed Polymerization of Monoalkyl Ethylene", Fontana et al., pp. (1688–1695).

Primary Examiner—Herbert Levine
Attorney, Agent, or Firm—Frank J. Jordan

[57] ABSTRACT

A process for preparing a colorless, odorless and transparent polymer oil having a low number average molecular weight, iodine value and viscosity and a high flash point, characterized by copolymerizing a mixture of n-pentene-1 and at least one other chain pentene in specific quantitative ratios in a Friedel-Crafts type catalyst and then hydrogenating the thus obtained liquid copolymer to a certain extent, and the polymer oil prepared thereby.

4 Claims, No Drawings

PROCESS FOR PREPARING POLYMER OILS AND POLYMER OILS PREPARED THEREBY

This invention relates to a process for preparing a novel polymer oil and to the polymer oil prepared thereby. More particularly, it relates to a process for the preparation of a novel polymer oil by copolymerizing pentenes comprising pentene-1 in the presence of a Friedel-Crafts type catalyst and then hydrogenating the thus produced liquid copolymer thereby obtaining the novel polymer oil, and to the novel polymer oil.

There have long been made many studies on processes for the cationic polymerization of unsaturated hydrocarbons in the presence of a Friedel-Crafts type catalyst, and it has been known that rubbery, resinous, liquid, gel-like or any desired polymers may be obtained by the selective use of polymerizing conditions such as a combination of catalyst and monomeric material. Typical of these polymers are polyisobutylene, petroleum resins and the like. The supply of hydrocarbon fractions obtained as the by-products from ethylene producing plants has recently been increased with the enlargement of the plants in scale or capacity and, in connection with one of the uses of these fractions, studies concerning the cationic polymerization thereof have come to be intensely made again. Among the fractions comprising the by-products, the $C_5$ fraction mainly includes, as the unsaturated hydrocarbon components, conjugated diolefins such as isoprene, 1,3-pentadiene and cyclopentadiene, as well as pentanes such as n-pentene-1, n-pentene-2, 2-methylbutene-1, 3-methylbutene-1 and 2-methylbutene-2. There have already been made many reports on processes for the cationic polymerization of the remaining portion obtained by separating the isoprene and cyclopentadiene components from the $C_5$ fraction. For example, U.S. Pat. No. 2,753,382 discloses a process for subjecting, in the presence of boron trifluoride, to polymerization the remainder of such a $C_5$ fraction, the remainder being obtained by the separation or removal of isoprene and cyclopentadiene from the $C_5$ fraction and being composed mainly of 1,3-pentadiene and pentenes, thereby to obtain a liquid polymer. The thus obtained liquid polymer exhibits a high iodine value since it contains a large proportion of 1,3-pentadiene comonomeric units. Thus the liquid polymer is useful as a synthetic oil substitute for natural drying oils such as linseed, safflower or soybean oil; however, it is unsuitable as a working fluid, such as a lubricating oil, functional oil or heat transfer medium, which is required to have stability. There is also known a process for the cationic polymerization of only n-pentene-1 which is one of the monoolefins contained in a $C_5$ fraction (Industrial and Engineering Chemistry Vol. 44, No. 7, 1953, pp. 1688 – 1695). However, a polymer or polypentene-1 obtained by the cationic polymerization of n-pentene-1 has a high molecular weight. It is greatly limited in its use as a working fluid due to its high molecular weight, and effective means are not found for producing polypentene-1 of a low molecular weight.

Attempts have thus been made by the present inventors to find a process for the cationic polymerization of n-pentene-1 to obtain a polymer having a lower molecular weight, and, as a result, it has been found that if n-pentene-1 is copolymerized with at least one other chain pentene, then a liquid copolymer having a number average molecular weight of from 300 to 1000 will be obtained. The liquid copolymer so obtained has a low iodine value because it contains unsaturated bonds in small amounts, and it is useful as a working fluid such as a lubricating oil, functional oil or heat transfer medium but it is not entirely satisfactory to use as a base material for cosmetic since it is somewhat unsuitable in color and irritant to human skin.

The primary object of this invention is to provide a process for the preparation of a novel polymer oil which is tasteless, odorless, colorless and transparent and has a low viscosity, a low pour point and, on the contrary, a high flash point in addition to having excellent thermal stability and water permeability.

Another object of this invention is to provide a polymer oil useful as a working fluid or a base material for cosmetics.

These objects of this invention are accomplished by copolymerizing a mixture containing 20 – 90% by weight of n-pentene-1 and 80 – 10% by weight of at least one other chain pentene, in the presence of a Friedel-Crafts type catalyst to produce a liquid copolymer having a number average molecular weight of from 300 to 1000 and then hydrogenating the thus produced liquid copolymer to obtain a desired novel polymer oil having a number average molecular weight of from 300 to 1000. (Since an increase of the liquid copolymer in number average molecular weight resulting from the hydrogenation is very small, the increase is neglected for the sake of brevity throughout the specification.) Thus, the polymer oil of this invention contains the units, in a partially or wholly hydrogenated form, derived from 20 – 90% by weight of n-pentene-1 and 80 – 10% by weight of at least one other chain pentene.

The monomers which may be used in the invention are chain pentenes containing n-pentene-1 in amounts of 20 – 90%, preferably 30 – 70%, by weight of the total monomers. The chain pentenes used herein include n-pentenes such as n-pentene-1, cis-pentene-2 and trans-pentene-2, and isopentenes such as 2-methylbutene-1, 2-methylbutene-2 and 3-methylbutene-1. The use of n-pentene-1 in amounts of more than 90% by weight of the total chain pentenes will give a polymer having an unduly high molecular weight, while that in amounts of less than 20% by weight of the total chain pentenes will give a polymer having an unduly low molecular weight; in any of these cases there will not be obtained a liquid polymer of a number average molecular weight of from 300 to 1000 suitable for use in the preparation of a polymer oil of this invention.

So long as a monomeric mixture of chain pentenes, which is useful in this invention, contains n-pentene-1 in amounts of 20 – 90% by weight of the mixture, the rest of the mixture may be composed of any chain pentenes other than n-pentene-1 in any ratios. In some cases, the monomeric mixture may be a two-component monomeric mixture consisting of n-pentene-1 and one chain pentene other than the former. The monomeric mixture may also contain, in addition to the chain pentenes, other unsaturated monomers which are copolymerizable with the chain pentenes, which includes isoprene, 1,3-pentadiene, butadiene, cyclopentadiene, cyclopentene, butene-1 and isobutene. The monomeric mixture, however, should not contain conjugated diolefins and/or cycloolefins in amounts exceeding 10%, preferably 5%, by weight of the total monomers since such a monomeric mixture containing more than 10% by weight of conjugated diolefins when polymerized will give a polymer wherein an intramolecular cyclizing reaction takes place thereby increasing the viscosity of the polymer, and such a mixture containing more than 10% by weight of cycloolefins when polymerized will give a polymer wherein cyclic materials are present in the molecule thereby causing undesirable phenomena such as an increase of the polymer in viscosity.

The chain pentenes according to this invention are polymerized in an inert diluent or without it in the presence of a Friedel-Crafts type catalyst. The Friedel-Crafts type catalysts used herein include customarily used halides of aluminum, iron, tin, boron and the like and further include sulfuric acid, hydrogen fluoride and the like, with aluminum chloride, aluminum bromide and other aluminum halides being the most recommendable.

The inert diluents used herein include butane, pentane, hexane, cyclohexane, dichloroethane and trichloroethylene, which compounds are aliphatic and alicyclic hydrocarbons and substitution products thereof. Aromatic hydrocarbons such as benzene and toluene, are not desirable as the diluent used herein since they will cause an alkylating reaction during the course of polymerization of the pentenes.

In the practice of this invention the other polymerizing conditions are not particularly limited and the polymerization is usually effected at temperatures of from −50° to 150°C and pressures of from 0 to 50 kg/cm$^2$ (gauge pressure) for 10 minutes to 10 hours. After the completion of the polymerization reaction, the reaction mixture is treated by a usual method to separate therefrom the used catalyst, unreacted monomers and the like thereby obtaining a liquid polymer. The liquid polymer so obtained is a somewhat light yellow colored, oily material having an iodine value of from about 20 to about 80 as determined by the Wijs method.

According to this invention the liquid polymer is then hydrogenated by the use of a known method to further decrease the unsaturated bonds present in the molecule thereby obtaining a desired final polymer oil. Hydrogenation of the liquid polymer is effected in, or without the use of, a solvent in the presence of a known catalyst for hydrogenation. The hydrogenation catalysts used herein include nickel, palladium, platinum, cobalt, osmium, rhenium, Raney nickel, nickel sulfide, nickel oxide, copper chromite, cobalt-molybdenum, chromium, molybdenum oxide, molybdenum sulfide, platinum oxide and cobalt oxide, as well as a combination of an organometallic compound and a fatty acid salt of a transition metal. Any of known hydrogenation catalysts may be used as such in the hydrogenation according to this invention. If desired, alumina, silica gel, various kinds of clays, charcoal and the like may also be used as a carrier for the hydrogenation catalysts.

The solvents which may be used herein include aliphatic, alicyclic and aromatic solvents such as pentane, hexane, heptane, octane, cyclohexane, decalin, tetralin, benzene, toluene and xylene. The hydrogenation is carried out in a batch or continuous fashion at temperatures ranging from room temperatures to temperatures below those at which the liquid polymers commence their thermal degradation, the hydrogenating temperatures being preferably between 100° and 300°C. The pressures used herein are not particularly limited and usually vary from normal atmospheric pressure to 300 atm. The reaction times vary from about 10 minutes to about 20 hours, preferably from about 10 minutes to about 3 hours.

After the completion of the hydrogenation reaction, the reaction mixture is freed from the used catalyst and solvent by a known usual method to obtain a colorless, transparent oily material. The polymer oil so obtained is a tasteless and odorless liquid having a number average molecular weight of about 300 – 1000, preferably 400 – 700 and an iodine value of not more than 10. The polymer oil further has properties such as an acid value of not more than about 0.02 mg/KOH, a saponification value of not more than 0.02 mg/KOH, a viscosity of 30 – 600 cps at 30°C, a Hazen number of not more than 50, a specific gravity of 0.80 – 0.90, a pour point of not higher than −30°C and a flash point of not lower than 150°C. In addition, the polymer oil is very excellently compatible with mineral, animal and vegetable oils such as liquid paraffin, olive oil, squalane, turtle oil, mink oil and camellia oil.

This polymer oil entirely eliminates drawbacks such as an unsatisfactory color and irritation to human skin, the drawbacks being those of the liquid polymer before being hydrogenated, and it is colorless and transparent and is excellent in affinity and spreadability (being well attached without stickiness to human skin and well spread thereon). The polymer oil further has nearly the same refractivity and water permeability as squalane which has been the most recommendable material as a base for cosmetics. These properties will be more remarkably apparent with a polymer oil portion obtained by subjecting the polymer oil to fractionation thereby selectively collecting a fraction boiling at approximately the same temperature as the hexamer of pentene (the fraction being hereinafter referred to as "fraction corresponding to the hexamer of pentene").

The polymer oils having the aforesaid properties as compared with liquid polybutene, liquid polypentadiene, liquid polyisoprene and the like in a hydrogenated state obtained by polymerization using a Friedel-Crafts type catalyst or a solid acid catalyst, are characterized by the following points for example:

1. Low pour point and, on the contrary, high flash point,
2. Low viscosity and
3. High water permeability.

The oily polymeric material obtained according to this invention is a novel polymer oil having the above mentioned characteristics and is very well balanced in its properties, whereas conventional non-drying oils have not only advantageous properties but also disadvantageous ones. The novel polymer oil may widely be used singly, jointly with at least one other non-drying oil and, if desired, further with conventionally used additives, such as a lubricating oil, grease, working oil, insulating oil, heat transfer medium, anti-freezing liquid, evaporation inhibiting liquid, base material for cosmetics, and the like.

This invention will be more fully explained by reference to the following examples.

REFERENCE EXAMPLE 1

To a 6-liter stainless steel reactor previously purged with nitrogen were added 1000 g of n-pentane, 650 g of n-pentene-1, 80 g of n-pentene-2, 150 g of 2-methylbutene-1, 40 g of 3-methylbutene-1 and 80 g of 2-methylbutene-2 to form a mixture. The resulting mixture was thoroughly agitated, combined five times with 2 g of aluminum chloride of a 40-mesh size at intervals of 30 minutes and then subjected to polymerization at 30°C for 2.5 hours. After the end of the polymerization, the reaction mixture was treated with activated clay, filtered and then dried in vacuo at 70°C thereby obtaining a light yellow colored, transparent liquid polymer in a yield of 83%. The polymer so obtained had an iodine value of 54.0 as determined by the method prescribed in JIS (Japanese Industrial Standard) K–5400 established on the basis of the Wijs method, and a number average molecular weight of 480 as measured by Vapor Pressure Osmometry (VPO).

REFERENCE EXAMPLE 2

A 6-liter stainless steel reactor previously purged with nitrogen, was charged with 800 g of benzene, 5 g of boron trifluoride.diethyl etherate and 0.6 g of water to form therein a mixture which was thoroughly agitated. This mixture was combined with a liquid mixture containing 2100 g of 1,3-pentadiene and 1400 g of n-pentane at a feeding rate of 500 – 1000 ml/hr and the resultant mixture was then polymerized at 40°C. After the end of the polymerization, the reaction mixture was treated with activated clay to remove the used catalyst therefrom, washed with methanol and then dried at 70°C in vacuo thereby to obtain a light yellow colored, transparent liquid polymer in a yield of 63%. The polymer so obtained had an iodine value of 270 and a number average molecular weight of 480.

EXAMPLE 1

To a 1-liter pressure-proof autoclave were added 500 g of the liquid polypentene prepared in Reference example 1 and thereafter 5 g of a stabilized nickel (supplied under the trade mark N–113 by Nikki Chemical Co., Ltd.) to form therein a mixture which was then reacted for 1 hour while kept at 180°C and 30 kg/cm$^2$ in a hydrogen atmosphere. Upon completion of the reaction, the reaction mixture was cooled to room temperatures, combined with 250 ml of n-hexane, thoroughly agitated, allowed to stand for a day and then treated to allow the supernatant liquid to be filtered thereby obtaining a filtrate. The filtrate was freed of the used n-hexane to obtain an oily material (Sample A). The liquid polypentadiene prepared in Reference example 2 was also treated in quite the same manner as the above mentioned liquid polypentene thereby to obtain an oily material (Sample B).

The thus obtained hydrogenated polypentene (Sample A) and polypentadiene (Sample B) as well as commercially available, hydrogenated polybutene (Sample C) were tested for their number average molecular weight, iodine value, pour point (as determined by JIS K–2269), flash point (as determined by JIS K–2274), viscosity at 30°C (by the use of B type viscosimeter) and Hazen number, to compare the thus obtained data among the three liquid polymers A, B and C. The results are shown in Table 1.

Table 1

| | Polymer oil of this invention | Comparative hydrogenated liquid polymer | |
|---|---|---|---|
| Sample | A | B | C* |
| Number average mol. wt. | 485 | 490 | 470 |
| Iodine value | 1.5 | 5 | 5 |
| Pour point (°C) | –50 | –55 | –25 |
| Flash point (°C) | 165 | 204 | 150 |
| Viscosity at 30°C (cps) | 85 | 225 | 240 |
| Hazen number | 50> | 50> | 50> |

*Produced by Idemitsu Petrochemical Co., Ltd.

From these results it is seen that the polymer oil of this invention as compared with the comparative hydrogenated liquid polymers, has a remarkably low viscosity although it has approximately the same molecular weight as the comparative polymers. It is also seen that the polymer oil of this invention is characterized by its low pour point and high flash point as compared with the known sample C. It has further been found that the polymer oil of this invention is entirely colorless and transparent and is perfectly free of some coloration which was observed in the liquid polymer from which the polymer oil was obtained by hydrogenation.

EXAMPLE 2

Sample A obtained in Example 1 was subjected to a test for its stability against oxidation by allowing the sample to stand in an air atmosphere at 165.5°C for 24 hours. The sample A after the test had an acid value of 0.02 (KOH mg/g polymer) which is the same as that of the original sample A. In addition, when sample A was subjected to a lacquering test no portion thereof was found attached to a varnish coated rod. From this result it is seen that the polymer oil of this invention is excellent in thermal stability.

REFERENCE EXAMPLE 3

To a 6-liter stainless steel reactor previously purged with nitrogen, were added 1000 g of n-pentane, 600 g of n-pentene-1 and 400 g of 2-methylbutene-1 to form therein a mixture which was then polymerized in the same manner as in Reference example 1 thereby obtaining a liquid polymer having an iodine value of 57.1 and a number average molecular weight of 450 in a yield of 93%.

REFERENCE EXAMPLE 4

A 1-liter autoclave previously purged with nitrogen was charged with 200 g of isoprene and 10 g of activated clay previously baked at 110°C for 2 hours. The resulting mixture in the autoclave was polymerized at 100°C for 15 hours. After the termination of the polymerizing reaction, the reaction mixture was filtered to remove the used catalyst therefrom and then dried at 70°C in vacuo thereby obtaining a liquid polymer having an iodine value of 275 and a number average molecular weight of 360 in a yield of 70%. The iodine value of this polymer is much lower than the theoretical value of 373 thereof, this indicating that the polymer has caused an intramolecular cyclizing reaction therein.

EXAMPLE 3

Each of the liquid polypentene prepared in Reference example 3 and the liquid polyisoprene prepared in Reference example 4 was hydrogenated in the same manner as in Example 1 thereby to produce the corresponding hydrogenated polymer. A portion of the hydrogenated polypentene so produced was fractionally distilled at 200°C under reduced pressure of 1 mm Hg thereby to obtain a fraction boiling at approximately the same temperature as the hexamer of pentene, in a yield of 27%.

The hydrogenated polypentene (Sample D), the fraction (Sample E) corresponding to the hexamer of pentene and the hydrogenated polyisoprene (Sample F), each obtained as mentioned above, as well as the hydrogenated polypentadiene (Sample B) prepared in Example 2, squalane and liquid paraffin, were tested for comparison to find their number average molecular weight, iodine value, refractivity, specific gravity and water-permeability. The results are shown in Table 2.

The test for water permeability was performed by introducing 10 g of water in a stainless steel testing receptacle having an inner diameter of 50 mm and a depth of 10 mm, applying each of the samples to a 15 mesh cloth of polyvinylidene chloride (Trademark: Saran) fibers in the amount of 150 mg/cm² so that a coating of the sample without voids created therein was formed on the cloth, closely enclosing the water containing testing receptacle with the sample coated cloth and then keeping the thus enclosed testing receptacle in a desiccator to find a decrease in the weight of the testing receptacle after the lapse of a predetermined time from the commencement of the test. The test results were expressed in terms of the weight of water permeated through the coated cloth per unit area of the cloth and per unit time, as calculated by the decrease in the weight of the receptacle.

Table 2

|  | Polymer oil of this invention | | Comparative (hydrogenated or non-hydrogenated) liquid polymer | | | |
| --- | --- | --- | --- | --- | --- | --- |
| Sample | D | E | B | F | Squalane | Liquid paraffin* |
| Number average mol. wt. | 455 | 420 | 490 | 370 | 420 | — |
| Iodine value | 1.3 | 1.0 | 5.0 | 6.4 | 1.8 | 1.8 |
| Refractivity ($n_D^{20}$) | 1.474 | 1.460 | 1.494 | 1.497 | 1.452 | 1.479 |
| Specific gravity ($d_4^{25}$) | 0.840 | 0.828 | 0.872 | 0.893 | 0.807 | 0.862 |
| Water permeability (g/hr.m²) | 5.5 | 8.7 | 3.1 | 2.7 | 5.6 | 3.0 |

*High White-350 (Trade mark) produced by Nippon Oil Co., Limited.

Table 2 indicates that the polymer oil of this invention has nearly the same properties as squalane which is the most excellent as a base material for cosmetics, and that it is a far more excellent base material for cosmetics as compared with liquid paraffin which has heretofore been used as a substitute for squalane and as compared with a hydrogenated liquid polyisoprene which has been considered suitable as a base material for cosmetics. Among the polymer oils of this invention, in particular, sample E, which is the fraction corresponding to hexamer of pentene, exhibits most nearly the same properties as squalane.

EXAMPLE 4

The polymer oils (Samples A, D and E) obtained in Examples 1 and 2 were each mixed with each of the various oils shown in Table 3 to find the compatibility between the oils mixed with each other, with the result being indicated in Table 3.

Table 3

| Sample | A | D | E |
| --- | --- | --- | --- |
| Squalane | O | O | O |
| Mink oil | O | O | O |
| Turtle oil | O | O | O |
| Olive oil | O | O | O |
| Camellia oil | O | O | O |
| Lanolin | O | O | O |
| Liquid paraffin | O | O | O |

The symbol "O" designates satisfactory uniform compatibility and transparency of the oils in mixture. From the result indicated in Table 3 it is seen that the polymer oils of this invention are very satisfactorily compatible with the various oils. It has further been found that the polymer oils of this invention when applied to human skin, exhibit an excellent affinity, keratolysis and spreadability with respect to human skin but do not exhibit any irritation to human skin.

What is claimed is:

1. A process for preparing a colorless, odorless and transparent polymer oil having a low number average molecular weight of 300 – 1000, low iodine value and low viscosity and a high flash point, comprising copolymerizing 20 – 90% by weight of n-pentene-1 and 80 – 10% by weight of at least one other chain pentene in the presence of a Friedel-Crafts type catalyst selected from the group consisting of halides of aluminum, iron, tin and boron, at a temperature of from −50° to 150°C and a gauge pressure of from 0 to 50 kg/cm² for 10 minutes to 10 hours thereby to produce a liquid polymer having a number average molecular weight of 300 – 1000 and then catalytically hydrogenating the thus produced liquid polymer at a temperature of from room temperature to a temperature below the temperature at which the liquid polymer commences its thermal degradation, at a pressure ranging from normal atmospheric pressure to 300 atm. for about 10 minutes to about 20 hours to an extent that the hydrogenated liquid polymer has an iodine value of not more than 10, thereby obtaining the desired polymer oil.

2. A process according to claim 1, wherein the other chain pentene is a member selected from the group consisting of cis-pentene-2, trans-pentene-2, 2-methylbutene-1, 2-methylbutene-2 and 3-methylbutene-1.

3. A process according to claim 1, wherein the temperature at which the hydrogenation is effected is in the range of from 100° to 300°C.

4. A colorless, odorless and transparent polymer oil made by the process of claim 1 and having a number average molecular weight of 300 – 1000, iodine value of not more than 10, acid value of not more than 0.02 mg/KOH, saponification value of not more than 0.02 mg/KOH, viscosity of 30 – 600 centipoises at 30°C, Hazen number of not more than 50, specific weight of 0.80 – 0.90, pour point of not higher than −30°C and flash point of not lower than 150°C.

* * * * *